United States Patent [19]
Hilt

[11] Patent Number: 5,332,484
[45] Date of Patent: Jul. 26, 1994

[54] APPARATUS AND PROCESS FOR THE LARGE SCALE SEPARATION AND RETRIEVAL OF PROTEINS FROM CELLULAR EXTRACTS

[75] Inventor: Craig R. Hilt, Milwaukee, Wis.

[73] Assignee: Hi-Tech Bio-Tech, Inc., Milwaukee, Wis.

[21] Appl. No.: 100,836

[22] Filed: Aug. 2, 1993

[51] Int. Cl.⁵ ............... G01N 27/26; G01N 27/447
[52] U.S. Cl. .................. 204/301; 204/182.8; 204/299 R
[58] Field of Search ............. 204/299 R, 182.8, 301

[56] References Cited

U.S. PATENT DOCUMENTS

| | | | |
|---|---|---|---|
| 3,384,564 | 5/1968 | Ornstein et al. | 204/182.9 |
| 3,579,433 | 5/1971 | Dahlgren | 204/299 R |
| 3,640,813 | 2/1972 | Nerenberg | 204/299 R |
| 3,988,230 | 10/1976 | Krotz | 204/182.1 |
| 4,204,929 | 5/1980 | Bier | 204/182.3 |
| 4,217,200 | 8/1980 | Kedem et al. | 204/301 |
| 4,617,102 | 10/1986 | Tomblin et al. | 204/182.8 X |
| 4,824,547 | 4/1989 | Zhang et al. | 204/299 R |
| 4,863,582 | 9/1989 | Wijangco et al. | 204/182.8 X |
| 4,877,510 | 10/1989 | Chen | 204/299 R |
| 4,883,597 | 11/1989 | Perlman | 210/640 |
| 4,897,306 | 1/1990 | Sugimoto et al. | 428/336 |
| 4,911,816 | 3/1990 | Love | 204/299 R |
| 4,957,613 | 9/1990 | Schuette | 204/299 R |
| 5,019,232 | 5/1991 | Wilson et al. | 204/182.8 |
| 5,073,246 | 12/1991 | Chu et al. | 204/182.8 X |
| 5,078,853 | 1/1992 | Manning et al. | 204/182.8 X |
| 5,112,460 | 5/1992 | Karger et al. | 204/182.8 |
| 5,139,637 | 8/1992 | MacConnell | 204/299 R |
| 5,149,418 | 9/1992 | Flesher | 204/182.8 X |
| 5,151,165 | 9/1992 | Huynh | 204/299 R |
| 5,164,057 | 11/1992 | Mori et al. | 204/299 R |

Primary Examiner—John Niebling
Assistant Examiner—John S. Starsiak, Jr.
Attorney, Agent, or Firm—Nilles & Nilles

[57] ABSTRACT

A protein purification system employs a pretreatment device which operates in concert with an electrophoretic purification device to separate and retrieve a large volume of highly purified proteins or other products from a mass of crude cellular extract. The pretreatment device causes the products to migrate horizontally through a series of cassettes and chambers at a relatively rapid rate determined by the size of the products to produce a crude mixture of products amenable to further purification. The purification device employs continuous vertical gel electrophoresis to separate the crude mixture into the highly purified products in large volumes and at a high rate without cooling. The electrophoretic purification device is also durable, easy to construct and use, and can be easily adjusted to vary the amount of matrix or gel through which the products must migrate, thus varying the amount of available purification.

18 Claims, 7 Drawing Sheets

APPARATUS AND PROCESS FOR THE LARGE SCALE SEPARATION AND RETRIEVAL OF PROTEINS FROM CELLULAR EXTRACTS

BACKGROUND OF THE INVENTION

1. Field of the Invention

The invention relates to protein separation and, more particularly, relates to an apparatus and process for the large scale separation and retrieval of proteins from a crude mixture of cellular matter.

2. Discussion of the Related Art

It is desirable for a wide variety of diagnostic and research procedures to separate and retrieve proteins from a cellular extract. The most popular technique heretofore used for such separation is known as continuous vertical gel electrophoresis or simply gel electrophoresis. Gel electrophoresis involves the separation and retrieval of enzymes or other proteins from complex mixtures by means of a differential migration of mixture components through a continuous gel medium under the imposition of an electric current. Examples of devices for performing gel electrophoresis are disclosed in U.S. Pat. No. 3,384,564 to Ornstein et al.; U.S. Pat. No. 3,579,433 to Dahlgren; and U.S. Pat. No. 4,877,510 to Chen. Each of these patents discloses a device employing lower and upper reservoirs defining lower and upper buffer chambers containing an ionic buffer solution and a conductive gel, respectively. The gel physically separates the two reservoirs. The upper buffer chamber of the device can be separated from the lower buffer chamber by at least one semipermeable membrane which permits the passage of ions but which prevents the passage of enzymes or other proteins being separated. When an electric current is conducted through such a device via positive and negative electrodes in the lower and upper buffer chambers, proteins migrate downwardly through the gel in the upper buffer chamber at different rates which are dependent upon the conductive properties of the individual proteins, thus separating into strata each containing one protein or one group of similar proteins. The thus stratified proteins continue to move downwardly through the gel in the upper buffer chamber until further movement is blocked by the semipermeable membrane, if present. The layers of proteins are then removed one by one, e.g., through pumping, before the next layer reaches the membrane.

Gel electrophoretic devices of the type described above typically can separate and retrieve proteins only on a very small scale and then at only a very slow pace. In fact, the typical device is capable of purifying only a few milligrams of proteins in several days or even weeks when used in conjunction with conventional partial purification procedures. This significantly hampers research or other procedures which require the retrieval of large volumes of proteins relatively quickly.

Proteins could not heretofore be retrieved at higher rates without encountering substantial difficulties. For instance, as the size of the electrophoretic apparatus is increased to accommodate greater volumes of cellular extracts, the surface area of the gel in the upper buffer chamber does not increase enough to permit sufficient heat transfer to dissipate satisfactorily the heat which is necessarily generated by the electrophoretic process. Since enzymes and other proteins are heat sensitive, the rate of electrophoresis must accordingly be maintained at or below a level above which the temperature of the enzymes or other proteins being retrieved may become denatured or otherwise inviable.

This problem can be alleviated to some extent by providing a cooling mechanism for reducing the temperature of the gel in the upper buffer chamber, but devices incorporating such cooling mechanisms are expensive and complex to manufacture and operate. In any event, even if an electrophoretic device were to be dimensioned to enhance heat transfer and/or cooled by a cooling device to facilitate larger scale electrophoresis without overheating the protein containing extract, the purification capacity of such a device would be inherently limited because the purification capacity of the gel is limited. This inherent clarification limitation necessarily delays the purification of proteins from the very crude extracts which serve as the base materials in typical electrophoretic processes.

Electrophoretic devices of the type described above also are operationally limited by the location of their negative electrodes. More specifically, such electrodes are typically immovably mounted within the upper buffer chamber or the associated funnel and thus require that the upper buffer chamber always be filled to a certain minimum level for operation.

OBJECTS AND SUMMARY OF THE INVENTION

It is therefore an object of the invention to provide a system which is capable of separating and retrieving a relatively large quantity of highly purified proteins from a crude cellular extract in a fraction of the time required for retrieval by conventional gel electrophoretic devices.

In accordance with a first aspect of the invention, this object is achieved by employing in concert 1) a horizontal pretreatment device employing the stepwise separation of a mass of cellular extract into a crude mixture of proteins amenable to further purification, and 2) a vertical electrophoretic device which receives as a base material the mixture produced by the pretreatment device and which employs continuous gel electrophoresis to purify further the proteins but which is capable of operating rapidly on a large scale. The pretreatment device preferably includes a receptacle for storing a conductive buffer solution and having a generally horizontal floor, first and second electrodes positioned in the receptacle, and a plurality of cassettes disposed in the receptacle between the first and second electrodes and extending upwardly from the floor. Each of the cassettes includes first and second semipermeable membranes and a layer of a conductive gel matrix sandwiched between the first and second membranes.

Another object of the invention is to provide an apparatus for continuous vertical gel electrophoresis which is simple and durable in construction and operation, which is capable of rapidly purifying proteins in large quantities, and which can be easily filled and operated with different levels of gel without fear of damaging the negative electrode.

In accordance with another aspect of the invention, this object is achieved by providing an electrophoretic device comprising a lower reservoir defining a lower buffer chamber for storing a first conductive medium, a first electrode in electrical communication with the interior of the lower buffer chamber, an upper reservoir defining an upper buffer champher for storing a second conductive medium, the upper buffer chamber being positioned in and extending above the lower buffer chamber, a second electros which can be placed in electrical communication with the interior of the upper buffer chamber, and a slide which is removably insertable in the upper buffer chamber. Preferably the second electrode is mounted on the slide and is positioned in the upper buffer chamber when the slide is inserted therein, and means are provided for adjusting the location of the second electrode in the upper buffer chamber. The means for adjusting preferably comprises means for adjusting the height of the slide with respect to the upper buffer chamber.

Still another object of the invention is to provide a method of separating and retrieving highly purified proteins from a crude cellular extract.

In accordance with another aspect of the invention, the method includes separating a mass of the crude cellular extract into a crude mixture of proteins amenable to further purification, and then separating and retrieving highly purified enzymes from the crude mixture through continuous vertical gel electrophoresis. The separation step includes inserting the mass into a receptacle between first and second ends extending from a generally horizontal floor, a plurality of cassettes being disposed in the receptacle between the first and second ends and extending upwardly from the floor, a conductive buffer solution being disposed in the receptacle between the cassettes; then conducting an electric current through the buffer solution to cause the proteins forming the mass to migrate from the first end of the receptacle to the second end; impeding the passage of groups of larger proteins through each of successive ones of the cassettes while permitting groups of smaller proteins to pass therethrough more rapidly, thus producing the crude mixture, and then removing the crude mixture from the receptacle.

The step of impeding preferably comprises, in the case of each of the cassettes, retaining the groups of larger enzymes in a conductive gel matrix sandwiched between two layers of semipermeable material.

Preferably, a further possible step comprises replacing the cassettes with cassettes having a matrix with a different percentage of gel following the pretreatment step, and then, prior to the electrophoretic step, reinsetting the crude mixture into the receptacle and repeating the pretreatment step.

Other objects, features, and advantages of the present invention will become more readily apparent to those skilled in the art from the following detailed description and the accompanying drawings. It should be understood, however, that the detailed description and specific examples, while indicating preferred embodiments of the present invention, are given by way of illustration and not of limitation. Many changes and modifications within the scope of the present invention may be made without departing from the spirit thereof, and the invention includes all such modifications.

BRIEF DESCRIPTION OF THE DRAWINGS

The preferred exemplary embodiment of the invention is illustrated in the accompanying drawings in which like reference numerals represent like parts throughout, and in which.

DETAILED DESCRIPTION OF THE PREFERRED EMBODIMENTS

Resume

Figure 1:
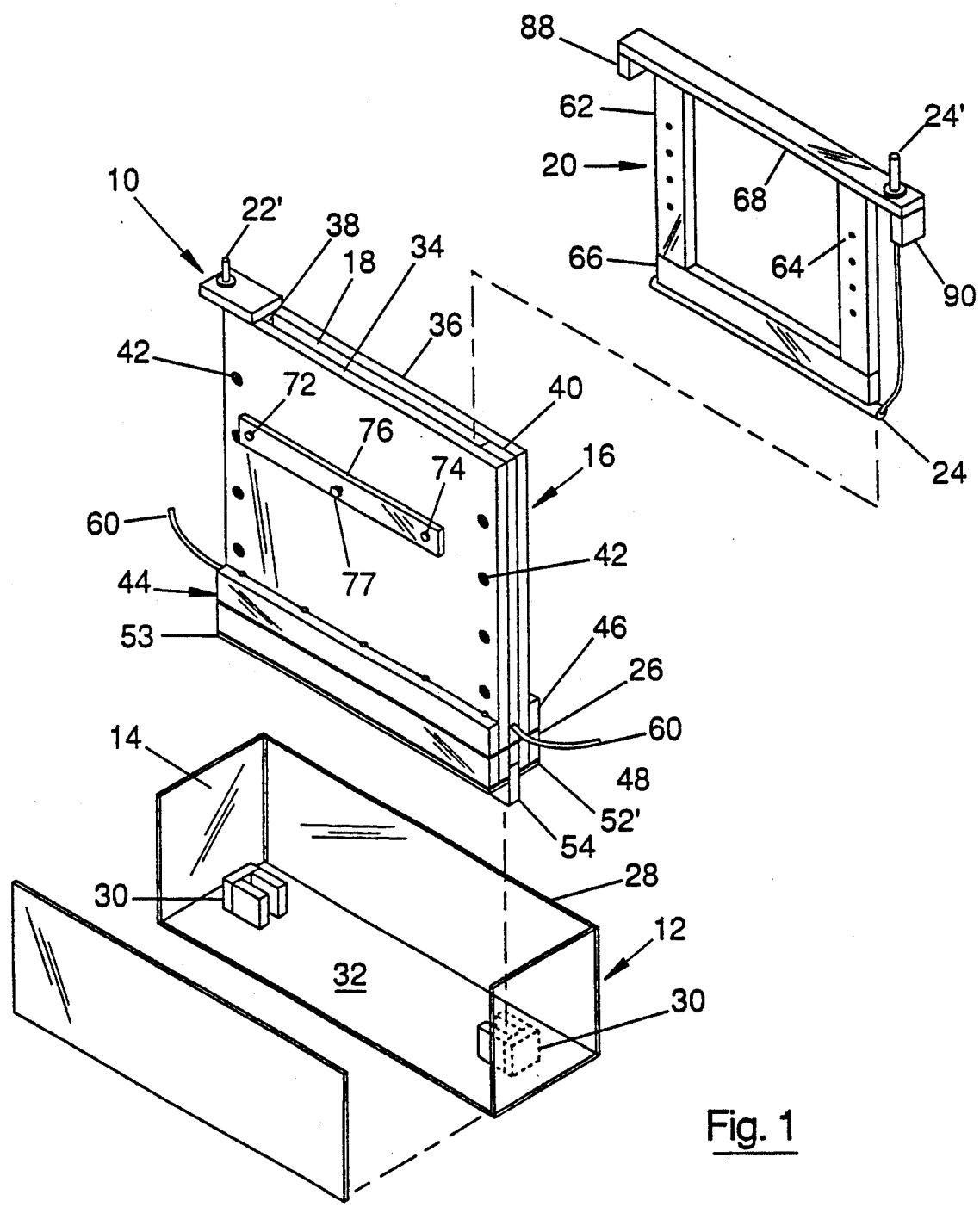
FIG. 1 is a perspective view of an electrophoretic device constructed in accordance with the present invention and usable as part of the inventive protein purification system.

Pursuant to the invention, a protein purification system employs a pretreatment device which operates in concert with an electrophoretic purification device to separate and retrieve a large volume of highly purified proteins from a mass of crude cellular extract. The pretreatment device causes the enzymes or other proteins being separated to migrate horizontally through a series of cassettes and chambers at a relatively rapid rate determined by the size of the proteins to produce a crude mixture of proteins amenable to further purification. The purification device employs continuous vertical gel electrophoresis to separate the crude mixture into the highly purified proteins in large volumes and at a high rate without extraneous cooling devices. The purification device is also durable, easy to construct and use, and can be easily adjusted to vary the amount of matrix or gel through which the proteins must migrate, thus varying the amount of available purification.

Construction and Operation of the Purification Device

Referring now to FIGS. 1-5, a purification device 10 constructed in accordance with the present invention is designed to quickly separate and retrieve relatively large volumes of highly purified enzymes, proteins, or other products from an extract using continuous vertical gel electrophoresis. These products will hereafter be collectively called "proteins" unless otherwise specified. Device 10 includes a lower reservoir 12 the interior of which defines a lower buffer chamber 14, an upper reservoir 16 the interior of which defines an upper buffer chamber 18, and a slide 20. A first (positive) electrode 22 is in electrical communication with the lower buffer chamber 14, and a second (negative) electrode 24 can be placed in electrical communication with the upper buffer chamber 18. The electrodes 22 and 24 are connected to suitable connectors 22' and 24' extending from the device 10. All components of the device 10 except for the electrodes 22 and 24 and the associated connectors are preferably constructed from a suitable plastic material which is non-conductive and which is not subject to corrosion by the gel or extract.

In use, a solution containing a product such as a cellular extract containing the proteins to be extracted is placed in the upper buffer chamber 18 above the gel matrix. The solution is then subjected to a dc electric current which is generated by a battery or any other suitable dc power source and conducted through the upper and lower buffer chambers. This current causes the proteins to stratify and to move downwardly through a gel matrix stored in the upper buffer chamber 18 at a rate determined by the size of the protein particles and by the electrical properties of the proteins. These stratified proteins are then separated from the gel in the upper buffer chamber 18 at the bottom 26 of the upper reservoir 16 one at a time and removed.

Lower reservoir 12 could be any device capable of supporting upper reservoir 16, of containing a conductive gel, and of communicating with the first electrode 22. In the illustrated embodiment, lower reservoir 12 takes the form of a generally rectangular box 28 having supports 30 mounted therein on which the upper reservoir 16 is mounted. The illustrated supports 30 comprise first and second sets of spaced C-brackets mounted on the floor 32 of the box 28 and spaced from one another so as to support the upper reservoir 16 as detailed below.

Upper reservoir 16 is designed so as to retain the gel in the upper buffer chamber 18 and so as to accommodate a relatively high volume of extract while still presenting sufficient surface area to permit electrophoresis of enzymes or other heat sensitive proteins without cooling devices. To this end, upper reservoir 16 is formed from opposed face plates 34 and 36 which are sealingly connected to one another in a spaced relation via opposed legs 38 and 40, the width of which define the thickness of upper buffer chamber 18. The face plates 34 and 36 and legs 38 and 40 may be connected by nylon bolts 42 or any other non-conductive connector.

Figure 2:
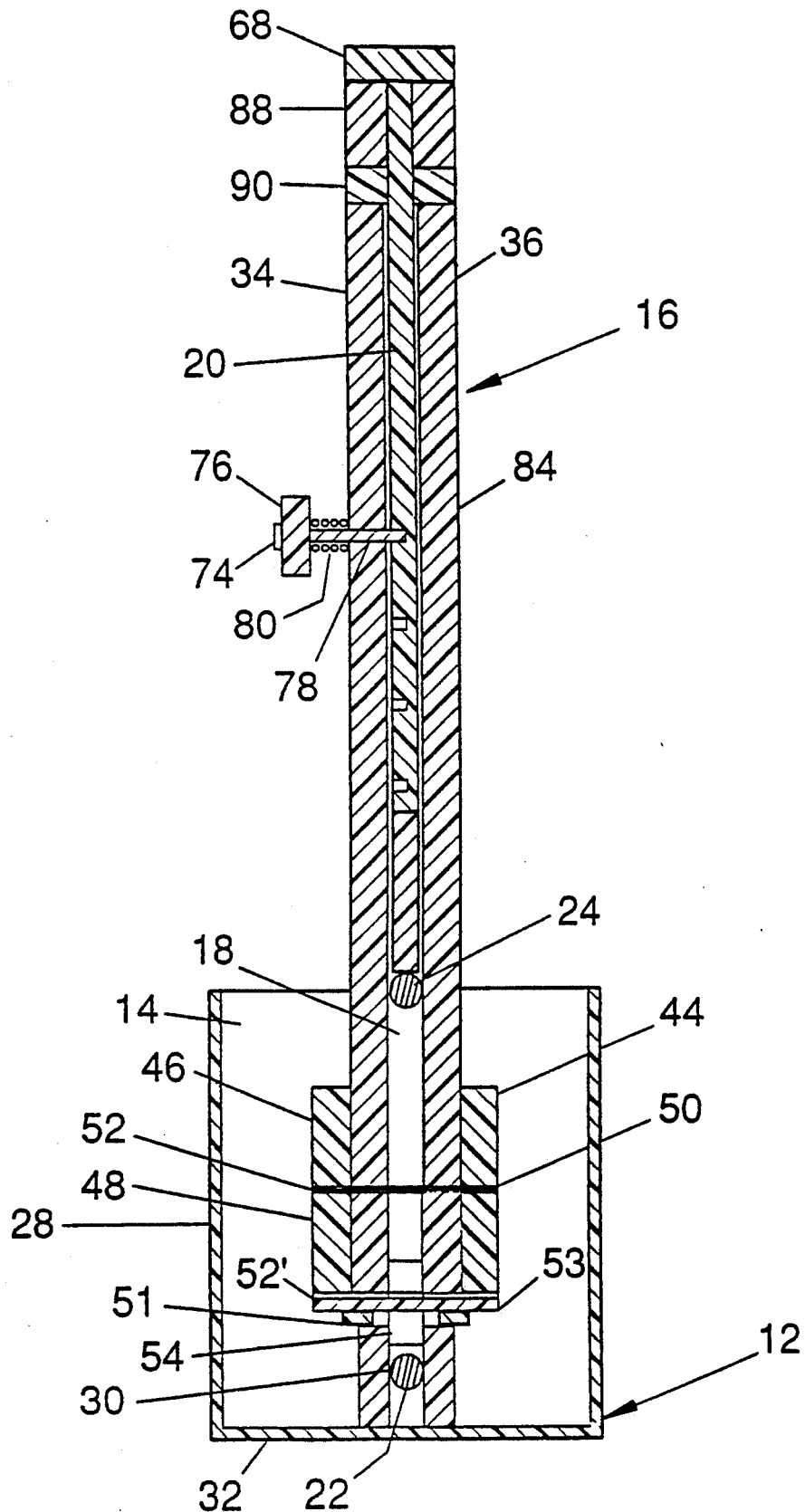
FIG. 2 is a sectional end view of the device of FIG. 1.
Figure 3:
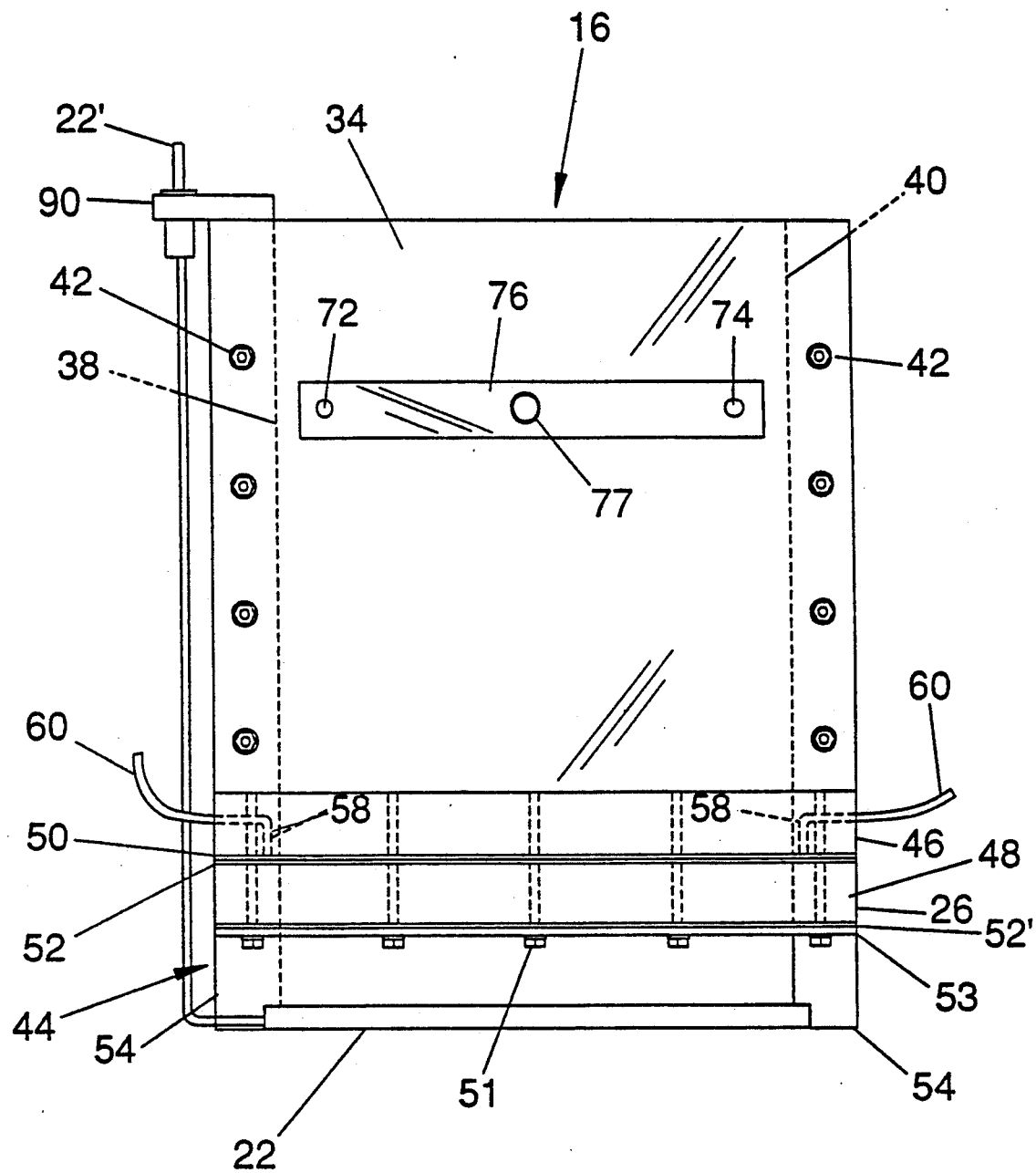
FIG. 3 is a sectional side view taken along the lines 3—3 in FIG. 2.

The bottom of the upper reservoir 16 is formed from a base 44 which supports the upper reservoir in the lower reservoir and which has membranes located therein which trap and permit retrieval of proteins. Base 44 is formed from upper and lower frames 46 and 48 sealed from each other by a gasket 49 and connected by bolts 51 so as to sandwich first and second membranes 50 and 52 therebetween. Tabs 54 extend downwardly from the lower frame 48 and are clamped in between the opposed sides of each of the C-brackets 30 in the lower reservoir 12 such that the bolts 51 extending from the bottom surface of the lower plate 48 rest upon the tops of C-brackets 30 as illustrated in FIG. 2. Tabs 54 also support the first electrode 22 so as to position it in the lower buffer chamber 14 during operation.

Figure 4:
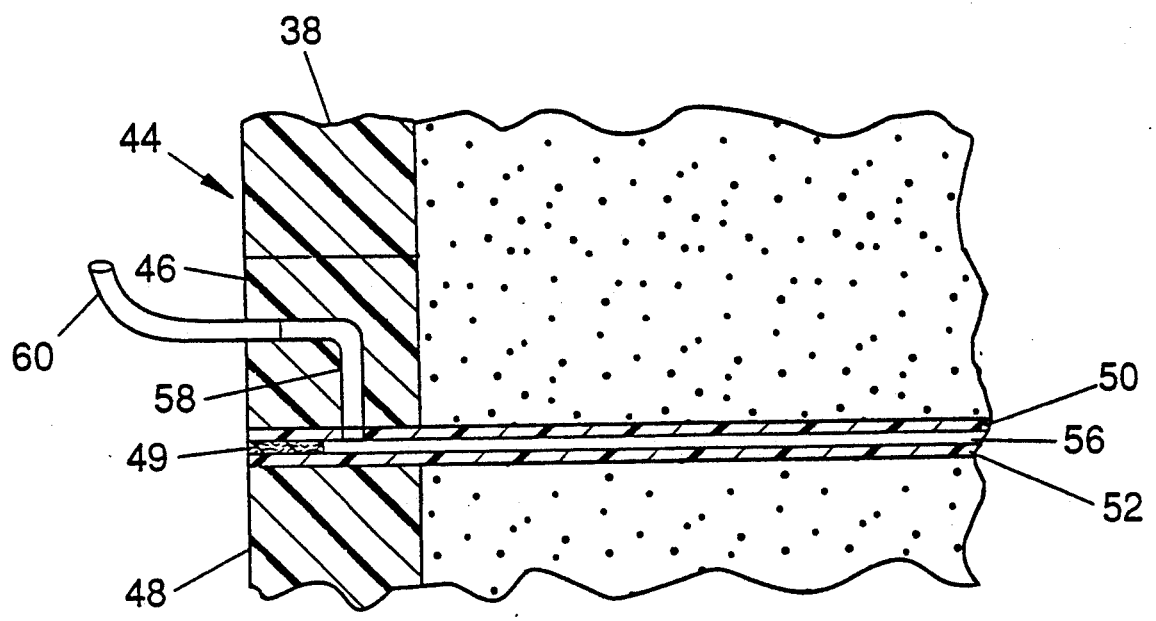
FIG. 4 is an enlarged view of a section of the device illustrated in FIGS. 1-3.
Figure 5:
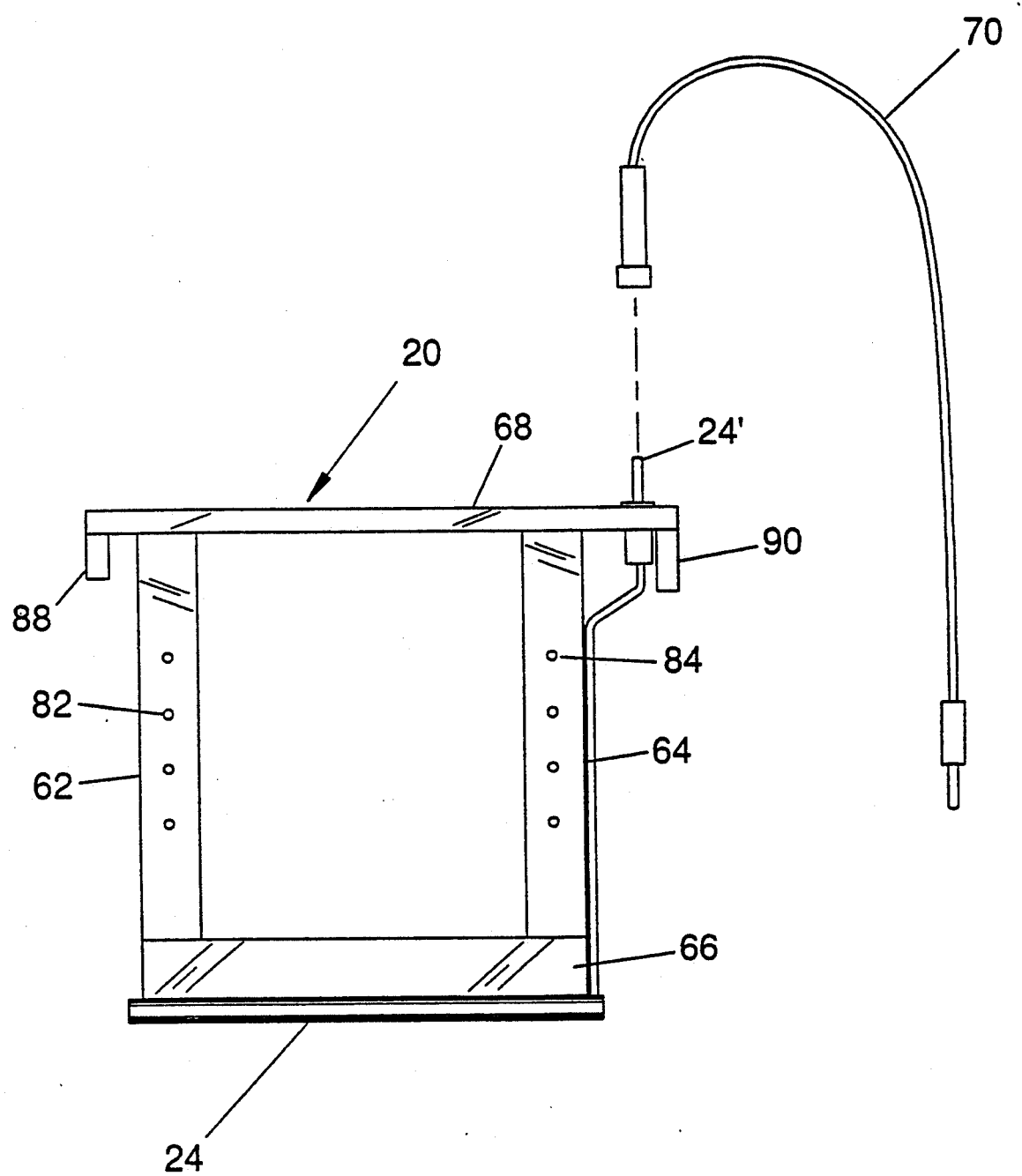
FIG. 5 is a side elevation view of a slide of the device of FIGS. 1-4.

Referring now especially to FIG. 4, the membranes 50 and 52 are designed to permit the passage of ions from the upper buffer chamber 18 to the lower buffer chamber 14 while at the same time separating the proteins from the gel in the upper buffer chamber 18 and permitting the removal of the proteins. Thus, upper membrane 50, which may more properly be considered a filter, is constructed from porous polypropylene or any other substance which permits the passage of protein containing fluids but which blocks the passage of gel. Lower membrane 52 is spaced from the upper membrane 50 to define a small chamber 56 therebetween and is formed from a semipermeable material which is, per se, well known and which permits its the passage of ions but which blocks the passage of proteins. Thus, during electrophoresis, proteins are trapped in the chamber 56 and can be pumped out of the chamber through channels 58 formed in the legs 38 and 40 and connected to hoses 60. A third membrane 52' (FIGS. 2 and 3) identical in construction to membrane 52 is provided at the bottom of the lower frame 48 of base 44 and held in place by a plate 53 to support gel located in a chamber beneath membrane 52 and forming an electrical link to the gel in lower buffer chamber 14.

Slide 20 is constructed from a simple frame dimensioned for insertion into the upper buffer chamber 18. The frame has opposed side walls 62 and 64 connected by a base 66 and a top plate 68. Electrode 24 is mounted on the bottom of base 66 and is coupled to the connector 24' which is formed on the top plate 68 and which mates with a suitable cable 70.

Slide 20 is designed to permit the vertical adjustment of the height of the second electrode 24 within the upper buffer chamber 18, thus permitting the variation of the amount of gel matrix in the chamber 18 and thus of the degree of available purification, while at the same time obviating the need for a fixed vertical electrode which may be subject to damage. This adjustment is preferably permitted by mounting the slide 20 on the upper reservoir 16 in a vertically adjustable manner. Any number of simple locking devices could be used for this purpose. In the illustrated embodiment, these devices take the form of detents 72 and 74 which are mounted on the face plate 34 of the upper reservoir 16 by a detent support bar 76, which sealingly extend through holes 78 in face 34 towards the legs 62 and 64 of the slide 20, and which are biased towards the slide 20 by tension springs 80 connected to the upper reservoir front face 34 and to the bar 76. A knob 77 may be fitted on the bar 76 to facilitate actuation. These detents can be received in any of a plurality of vertically spaced holes 82 and 84 formed in the respective legs 62 and 64 of the slide 20 to support the slide in the upper reservoir 18 in a vertically adjustable manner. Stops 88 and 90 are provided on the slide 20 to limit the depth of insertion of the slide into the upper buffer chamber 18, with the stop 88 resting on the plate supporting the connector 22' and the stop 90 resting on the upper surface of reservoir faces 34 and 36.

The electrophoretic device 10 operates as follows:

First, to prepare the device for use, the upper chamber 18 is partially filled with a conductive polyacrylamide or agarose gel, the lower buffer chamber 14 is filled with a buffer solution, and the slide 20 is positioned in the upper buffer chamber 18 and positioned at the desired height by the detents 72 and 74. The level of gel in upper buffer chamber 18 and thus the location of the slide 20 within the chamber 18 will depend upon the degree of purification required. A buffer solution and the extract containing the proteins to be purified is then poured on top of the gel in the upper buffer chamber 18. A dye should also be poured into the mixture to petit visual observation of the stratification of proteins during electrophoresis.

Next, electrophoresis is initiated by conducting a dc electric current through electrodes 22 and 24. The proteins migrate downwardly through the gel matrix in the upper buffer chamber 18 at different rates determined by the size and conductivity of the respective proteins in a manner which is, per se, well known, thus resulting in a stratification effect in which the proteins are purified as they exit the bottom of the upper buffer chamber 18. Each layer of proteins migrates through the upper membrane or filter 50, is trapped in the chamber 56 located between the upper and lower membranes 50 and 52, and is removed via channels 58 and hoses 60 under the action of a pump or any other suitable device before the next layer reaches the chamber.

Because the upper buffer chamber 18 is much wider than it is thick, it presents a large surface area for heat transfer and thus can accommodate large volumes of extract without overheating and denaturing the enzymes or other proteins in the extract. Devices heretofore available could purify only minuscule quantities of extract or required complex cooling devices to prevent denaturing the enzymes or other proteins being purified.

The purification capabilities of the device 10 can be increased still further if the proteins are pretreated by being partially purified or separated from one another prior to operation of the device. A system and process for the crude separation of a large mass of cellular extract into a mixture of proteins amenable to further purification in device 10 will now be described.

Description and Operation of Pretreatment Device

Figure 6:
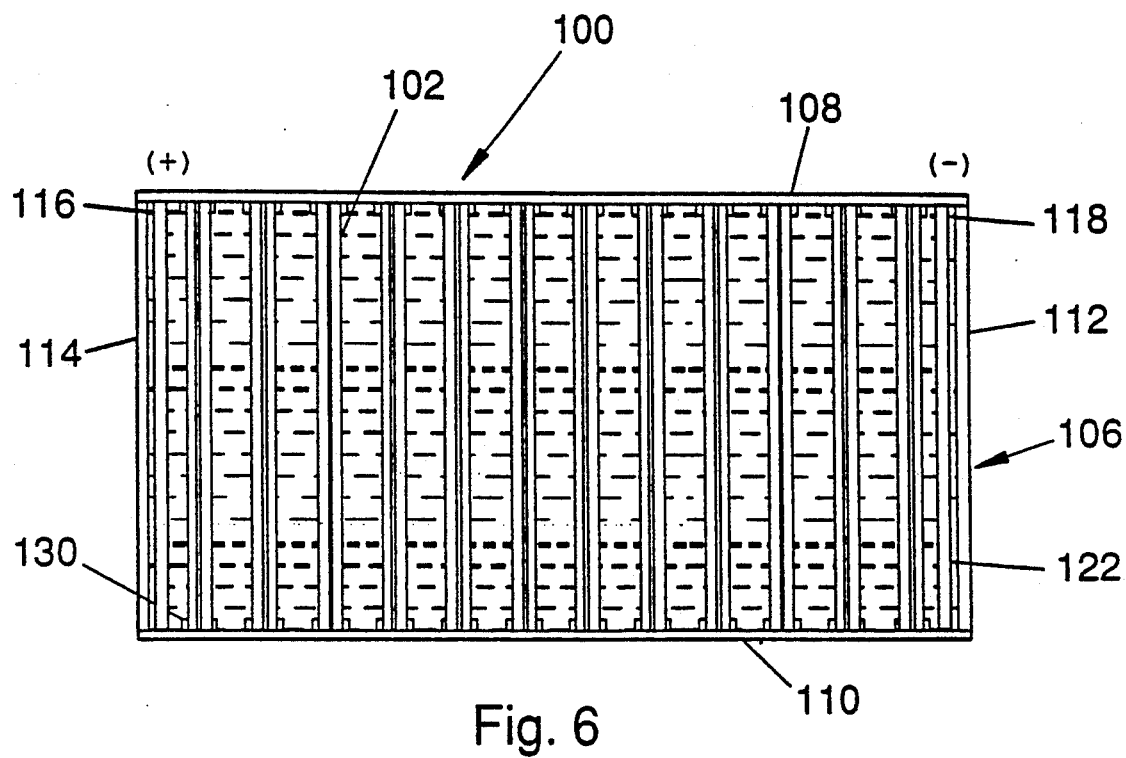
FIG. 6 is a plan view of a pretreatment device usable with the purifier of FIGS. 1-6.
Figure 7:
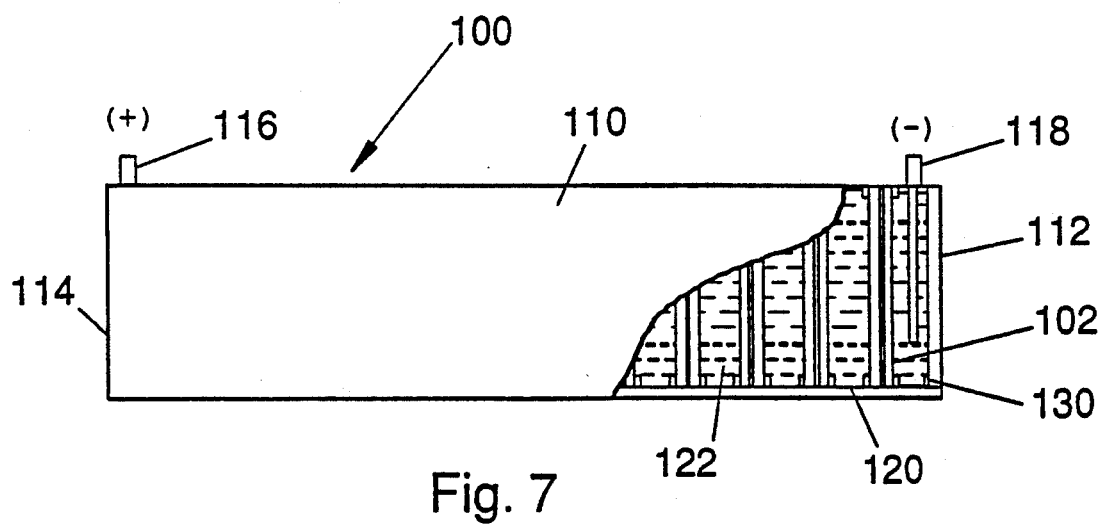
FIG. 7 is a sectional elevation view of the separator of FIG. 6.
Figure 8:
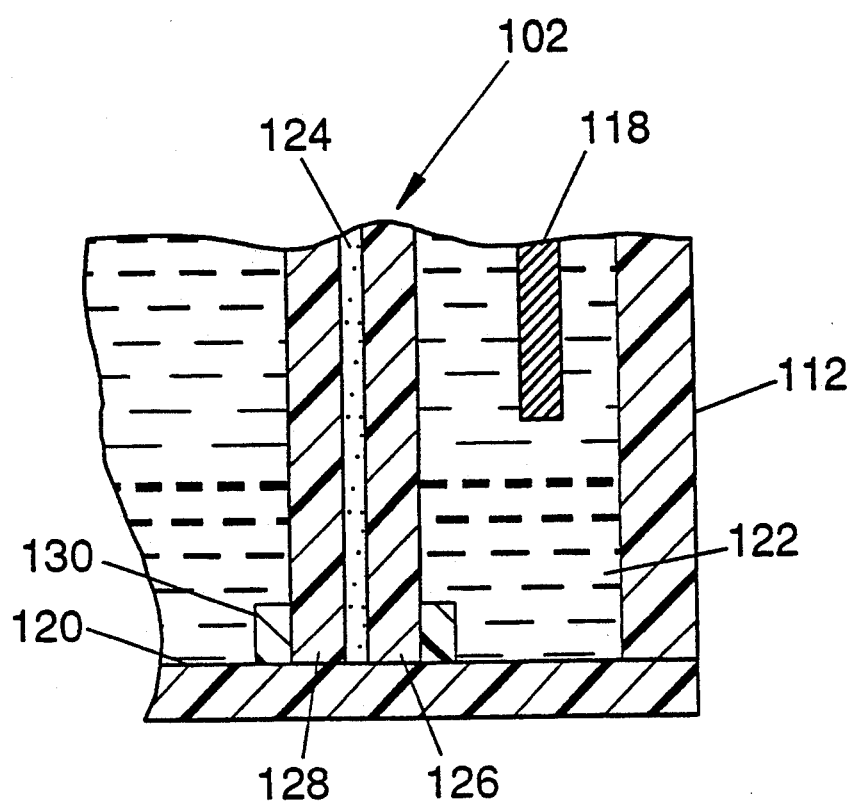
FIG. 8 is a sectional elevation view of a portion of the separator of FIGS. 6 and 7.

Referring now to FIGS. 6–8, the pretreatment device 100 is designed to separate a crude mixture of proteins from a mass of cellular extract by causing the mixture to migrate horizontally through a plurality of narrow separation zones in a stepwise fashion. To this end, the device 100 employs a plurality of cassettes 102 extending upwardly from a floor 120 of a receptacle 106 having side walls 108 and 110 and end walls 112 and 114. Positive and negative electrodes 116 and 118 are positioned in the receptacle 106 adjacent the end walls 112 and 114 and supply a dc electric current to a buffer solution 122 located in the receptacle 106.

Each of the cassettes 102 is designed to impede the passage of larger particles while permitting the more rapid passage of smaller, more conductive particles therethrough while the particles migrate through the receptacle from the first end 112 to the second end 114 under the imposition of the electric current supplied by the electrodes 116 and 118. To this end, each cassette 102 includes a layer of a polyacrylamide or agarose gel matrix 124 sandwiched between two layers 126 and 128 of porous polypropylene or any other suitable material of the type described above which permits the passage of extract but which blocks the passage of gel. The layers 124 of gel impede migration of proteins therethrough in the same manner as the gel in the upper buffer chamber 118 of electrophoretic device 10 impedes the passage of proteins, but, because each layer is relatively thin, permits the passage of a much higher voluble of protein albeit with much lower purification. Thus, different crude mixtures each containing a class of proteins reach the end 114 of receptacle 106, where they can be removed one at a time via a pipet or any other suitable device. The process performed by pretreatment device 100 is thus more akin to chromatography than to conventional continuous vertical gel electrophoresis.

Pretreatment device 100 is preferably designed to be adjustable so as to provide varying levels of purification. To this end, the cassettes 102 are detachably mounted in the receptacle 106 via suitable clamps 130 or any other suitable devices permitting easy retraction and replacement. Thus, more or fewer cassettes 102 could be employed and/or cassettes with lower or higher percentages of gel could be employed to provide lower or higher degrees of purification. This configuration also permits the implementation of a multi-pass process prior to further purification in electrophoretic device 10 by first running an extract through the pretreatment device 100 using cassettes 102 having a relatively low percentage of gel to obtain a first mixture of interest, by replacing the cassettes with ones having a higher percentage of gel, and by running the first mixture through the pretreatment device a second time to obtain a second mixture.

After pretreatment in the device 100 in either a single or multi-pass process, the crude mixture of interest obtained at the end of the process is now amenable to further purification by a more conventional continuous vertical gel electrophoretic process which can be performed relatively rapidly because much less purification is required to retrieve highly purified proteins. This shorter retention time permits the purification of higher volumes of extract in the electrophoretic device without cooling the device.

The devices 10 and 100, if used in concert, can retrieve large volumes of highly purified proteins from a mass of cellular extract in only a few hours without cooling. Heretofore available processes, on the other hand, would require several weeks or even longer to purify the same volume of proteins by conventional chromatography.

Many changes and modifications could be made to the present invention without departing from the spirit and scope thereof. For instance, the devices 10 and 100 need not necessarily be used in concert but could each be used either alone or in combination with other known devices. Moreover, although the examples detailed above were limited to the separation of enzymes or other proteins, the devices 10 and 100 could be used to purify any product which can be stratified as it moves through a conductive gel or other matrix under the imposition of an electric current. Other changes and modifications which could be made to the invention without departing from the spirit and scope thereof will become more readily apparent from a reading of the appended claims.

I claim:
1. An electrophoretic device comprising:
   A. a lower reservoir defining a lower buffer chamber for storing a first conductive medium;
   B. a first electrode in electrical communication with the interior of said lower buffer chamber;
   C. an upper reservoir defining an upper buffer chamber for storing a second conductive medium, said upper buffer chamber being positioned in and extending above said lower buffer chamber;
   D. a second electrode which can be placed in electrical communication with the interior of said upper buffer chamber; and
   E. a slide which is removably insertable in said upper buffer chamber.

2. A device as defined in claim 1, wherein said second electrode is mounted on said slide and is positioned in said upper buffer chamber when said slide is inserted therein.

3. A device as defined in claim 2, further comprising means for adjusting the location of said second electrode in said upper buffer chamber.

4. A device as defined in claim 3, wherein said means for adjusting comprises means for adjusting the height of said slide with respect to said upper buffer chamber.

5. A device as defined in claim 4, further comprising a stop for limiting the degree at which said slide may be inserted into said upper buffer chamber.

6. A device as defined in claim 1, further comprising first and second semipermeable membranes separating said upper buffer chamber from said lower buffer chamber, said first membrane being located above said second membrane and permitting the passage of ions and proteins but blocking the passage of gel, said second membrane permitting the passage of ions but blocking the passage of proteins.

7. A device as defined in claim 6, wherein a passage is formed between said first and second membranes, and further comprising means, communicating with said passage, for removing proteins from said passage.

8. A pretreatment device for separating a mass of cellular extract into a crude mixture of proteins amenable to further purification, said device comprising:
   A. a receptacle for storing a conductive buffer solution, said receptacle having a generally horizontal floor;
   B. first and second electrodes positioned in said receptacle; and
   C. a plurality of cassettes disposed in said receptacle between said first and second electrodes and extending upwardly from said floor, each of said cassettes including
      (1) first and second semipermeable membranes, and
      (2) a layer of a conductive gel matrix sandwiched between said first and second membranes.

9. A device as defined in claim 8, wherein each of said first and second membranes is formed from a layer of a porous nonwoven substance.

10. A device as defined in claim 8, wherein said gel comprises one of polyacrylamide gel and agarose gel.

11. A device as defined in claim 8, wherein said cassettes are detachably mounted in said receptacle so as to be readily replaceable with cassettes having different percentages of said gel.

12. A system for separating and retrieving highly purified proteins from a crude cellular extract, comprising:
   A. a pretreatment device for separating a mass of said crude cellular extract into a crude mixture of proteins amenable to further purification, said device including
      (1) a receptacle for storing a conductive buffer solution, said receptacle having a generally horizontal floor;
      (2) first and second electrodes positioned in said receptacle; and
      (3) a plurality of cassettes disposed in said receptacle between said first and second electrodes and extending upwardly from said floor, each of said cassettes including
         (A) first and second semiperlneable membranes, and
         (B) a layer of a conductive gel matrix sandwiched between said first and second membranes; and
   B. an electrophoretic device which receives said crude mixture of proteins from said pretreatment device and which separates and retrieves said highly purified proteins from said mixture.

13. A system as defined in claim 12, wherein said electrophoretic device comprises
   A. a lower buffer chamber for storing a first conductive medium;
   B. a first electrode in electrical communication with the interior of said lower buffer chamber;
   C. an upper buffer chamber for storing a second conductive medium, said upper buffer chamber being positioned in and extending above said lower buffer chamber;
   D. a second electrode which can be placed in electrical communication with the interior of said upper buffer chamber; and
   E. a slide which is removably insertable in said upper buffer chamber.

14. A system as defined in claim 13, wherein said electrophoretic device further comprises means for adjusting the location of said second electrode in said upper buffer chamber.

15. A system as defined in claim 14, wherein said means for adjusting comprises means for adjusting the height of said slide with respect to said upper buffer chamber.

16. A method of separating and retrieving highly purified proteins from a crude cellular extract, comprising:
   A. separating a mass of said crude cellular extract into a crude mixture of proteins amenable to further purification, said separation step including
      (1) inserting said mass into a receptacle between first and second ends extending from a generally horizontal floor, a plurality of cassettes being disposed in said receptacle between said first and second ends and extending upwardly from said floor, a conductive buffer solution being disposed in said receptacle between said cassettes, then
      (2) conducting an electric current through said buffer solution to cause said mass to migrate from said first end of said receptacle to said second end,
      (3) impeding the passage of groups of larger proteins through each of successive ones of said cassettes while permitting groups of smaller proteins to pass therethrough more rapidly, thus producing said crude mixture, and then
      (4) removing said crude mixture from said receptacle; and then
   B. separating and retrieving highly purified enzymes from said crude mixture through continuous vertical gel electrophoresis.

17. A method as defined in claim 16, wherein said step of impeding comprises, in the case of each of said cassettes, retaining said groups of larger enzymes in a conductive gel matrix sandwiched between two layers of semipermeable material.

18. A method as defined in claim 17, further comprising replacing said cassettes with cassettes having a different percentage of gel following said step (A), and then, prior to said step (B), reinsetting a portion of said crude mixture into said receptacle and repeating said steps (2)–(4).

* * * * *